US006833475B2

(12) United States Patent
Sinha et al.

(10) Patent No.: US 6,833,475 B2
(45) Date of Patent: Dec. 21, 2004

(54) HEPTANONIC ACID AND FURANONE COMPOUNDS AND COMPOSITIONS

(75) Inventors: Arun Kumar Sinha, Himachal Pradesh (IN); Bhupendra Prasad Joshi, Himachal Pradesh (IN); Ruchi Dogra, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/449,098

(22) Filed: Jun. 2, 2003

(65) Prior Publication Data

US 2003/0212281 A1 Nov. 13, 2003

Related U.S. Application Data

(62) Division of application No. 09/815,335, filed on Mar. 23, 2001, now Pat. No. 6,579,992.

(51) Int. Cl.$^7$ ............................................. C07C 59/147
(52) U.S. Cl. ...................... 562/577; 426/590; 426/592; 426/660
(58) Field of Search .......................... 562/577; 426/590, 426/592, 660

(56) References Cited

U.S. PATENT DOCUMENTS

| 3,383,412 A | 5/1968 | Wellman et al. |
| 3,530,149 A | 9/1970 | Fiecchi |
| 5,296,220 A | 3/1994 | Roelofs et al. |

OTHER PUBLICATIONS

Chem Abs 110:63501 Nishimura, O et al, Development in Food Science (1988) 375–86.*
Coello et al., "Fermentation of White Wines in the Presence of Wood Chips of American and French Oak", J. Agric. Food Chem., 2000, vol. 48, pp. 885–889.
Masson et al., "Identification of a Precursor of β–Methyl–γ–octalactone in the Wood of Sessile Oak", J. Agri. Food Chem., 2000, vol. 48, pp. 4306–4309.
Marino et al., "Stereospecific Synthesis of γ–Butyrolactones from Acyclic Vinyl Sulfoxides: An Asymmetric Synthesis of Optically Pure Oak Lactones", 1985, vol. 26, No. 44, pp. 5381–5384.
Otsuka et al., "Presence and Significance of Two Diastereomers of β–Methyl–γ–octalactone in Aged Distilled Liquors", Agri. Biol. Chem., 1974, vol. 38, No. 3, pp. 485–490.
Kunz et al., "A Chelate–Controlled Route to Disubstituted and Tetrasubstituted γ–Lactones Stereoselectivity in Lewis Acid Promoted Additions to Chiral Methyl β–Formylcarboxylates", 1989, Chem. Ber., vol. 122, pp. 2165–2175.
Taber et al., "The 2–Hydroxycitronellols, Convenient Chirons for Natural Products Synthesis", American Chemical Society, 1994, vol. 59, pp. 4004–4006.

Suzuki et al. "Concise Enantiospecific Syntheses of (+)–Eldanolide and (–)–cis–Whisky Lactone", Tetrahedron Letters, 1992, vol. 33, No. 34, pp. 4931–4932.
Hoppe et al., "Asymmetric Homoaldol Reaction by Enantioselective Lithiation of a Prochiral 2–Butenyl Carbamate", Angew Chem. Int. Ed. Engl., 1989, vol. 28, No. 2, pp. 69–71.
Bloch et al., "Synthesis of Both Enantiomers of γ–Substituted α,β–Unsaturated γ–Lactones", J. Org. Chem., 1987, vol. 52, pp. 4603–4605.
Ebata et al., "Synthesis of (+)–Trans–Whisky Lactone, (+)–Trans–Cognac Lactone and (+)–Eldanolide", Heterocycles, 1990, vol. 31, No. 9, 1585–1588.
Waterhouse et al., "Oak Lactone Isomer Ratio Distinguishes Between Wines Fermented in American and French Oak Barrels", J. Agri. Food Chem., 1971–1974, vol. 42, No. 9.
Reissig et al., "Ester Groups as Effective Ligands in Chelate–Controlled Additions of Cuprates and Grignard Reagents to Chiral β–Formyl Esters", J. Org. Chem., 1993, vol. 58, pp. 6280–6285.
Lo et al., "Applications of Planar–Chiral Heterocycles in Enantioselective Catalysis: Cu(l)/Bisazaferrocene–Catalyzed Asymmetric Ring Expansion of Oxetanes to Tetrahydrofurans", Tetrahedron, 2001, vol. 57, pp. 2621–2634.
Tanaka et al., "Whisky Lactone Precursors from the Wood of *Platycarye strobilacea*", J. Nat. Prod, 1996, vol. 59, pp. 997–999.
Takahata et al., "New Entry to Chiral Butenolide Synthons. Application to Expeditious Syntheses of (+)–Nephrosteranic Acid, (+)–trans–Whisky Lactone, and (+)–trans–Cognac Lactone", Tetrahedron, 1994, vol. 35, No. 24, pp. 4123–4124.
Ito et al., "Chiral Bipyridine and Biquinoline Ligands: Their Asymmetric Synthesis and Application to the Synthesis of trans–Whisky Lactone", Tetrahedron, 1996, vol. 52, No. 11, pp. 3905–3920.
Nishikori et al., "A Short–Step Synthesis of trans–Whisky Lactone by an Asymmetric Michael Reaction", Tetrhedron: Asymmetry, 1998, vol. 9, pp. 1165–1170.

* cited by examiner

Primary Examiner—Paul J. Killos
(74) Attorney, Agent, or Firm—Foley & Lardner LLP

(57) ABSTRACT

A natural inexpensive acyclic monoterpene ketone (dihydrotagetone) of formula (4), isolated from the oil of *Tagetes* sp., was smoothly oxidized with meta-periodate/potassium permanganate into 2,6-dimethyl-4-oxo-heptanoic acid of formula (3), the reduction of 3 with metal hydride such as sodium borohydride or lithium aluminium hydride provided 4-hydroxyacid of formula (2) which on without isolation undergone lactonisation in acidic medium furnished two chiral centered 5-isobutyl-3-methyl-4,5-dihydro-2(3H)-furanone of formula (1) as an analogue of whisky lactone 5-butyl-4-methyl-4,5-dihydro-2(3H)-furanone of formula (1a) responsible for high quality of alcoholic beverage (whisky, wine, brandy and scotch), in addition, coconut flavoured 5-butyl-4-methyl-4,5-dihydro-2(3H)-furanone of formula (1) is also as an analogue of coconut aldehyde (γ-nonalactone, F.E.M.A. No. 2751) of formula (1b) which is responsible for flavouring a wide range of food stuffs including baked goods and confectionery.

6 Claims, 6 Drawing Sheets

H NMR (300 MHz) spectra of 2,6-dimethyl-4-oxo-heptanoic acid in CDCl

H NMR (300 MHz) spectra of 5-isobutyl-3-methyl-4,5-dihydro-2(3H)-furanone

C-NMR (75.4 MHz) spectra of 5-isobutyl-3-methyl-4,5-dihydro-2(3H)-furanone in CDCl3.

GC of 5-isobutyl-3-methyl-4,5-dihydro-2(3H)-furanone

Mass spectra of 5-isobutyl-3-methyl-4,5-dihydro-2(3H) furanone.

HEPTANONIC ACID AND FURANONE COMPOUNDS AND COMPOSITIONS

This is a divisional of application Ser. No. 09/815,335, filed Mar. 23, 2001, now U.S. Pat. No. 6,579,992.

FIELD OF THE INVENTION

This invention relates to a novel method for converting dihydrotagetone, a bifunctional acyclic monoterpene ketone, isolated from plant species of *Tagetes* species into coconut flavoured 5-isobutyl-3-methyl-4,5-dihydro-2(3H)-furanone with two chiral centers of formula (1). Interestingly, the compound (1) is found as a novel analogue of whisky lactone (also named as Querecus lactone or oak lactone) of formula (1a), which is contained, for example, in high quality alcoholic beverages (Napolean whisky, Jamaica and cognac etc), as fragrance ingredient, in insect pheromones and several natural products containing this structural moiety. Moreover coconut flavoured compound (1) is also an analogue of coconut aldehyde (γ-nonalactone or aldehyde C-18, F.E.M.A. No. 2751) of formula (1b) which is responsible for flavouring a wide range of food stuffs including baked goods and confectionery.

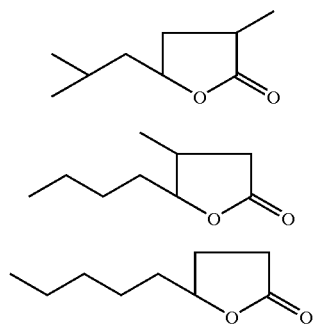

(1) No. of chiral centers=2; (1a) No. of chiral centres=2; (1b) No. of chiral center=1

| Mol. Formula = $C_9H_{16}O_2$ | Mol. Formula = $C_9H_{16}O_2$ | Mol. Formula = $C_9H_{16}O_2$ |
| --- | --- | --- |
| Mol. wt. = 156 | Mol. wt. = 156 | Mol. wt. = 156 |
| Aroma = Coconut like | Aroma = Coconut like | Aroma = Coconut like |

The present invention also relates to 2,6-dimethyl-4-oxo-heptanoic acid of formula (3) not only as a precursor for the synthesis of whisky lactone of formula (1a) but also as a novel analogue of 2,6-dimethyl-5-oxo-heptanoic acid (a constituent of well known essential oil of *Mentha x piperita*) which has wide applications in flavouring food stuffs, soft and alcoholic beverages, perfumery and pharmaceutical industries.

BACKGROUND OF THE INVENTION

A wide-spread class of γ-butyrolactones (also known as dihydro-2(3H)-furanone or 4-butanolide or tetrahydro-2-furanone) were first synthesized in 1884 via internal esterfication of 4-hydroxybutyric acid. These important lactones exhibit very intensive and pleasant fruity aroma and can be easily transformed into other useful products e.g. furans, cyclopentenones, butenolides and pyrrolidones (Freudenberger, D., Wunder, F. and Fernholz, H., U.S. Pat. No. 4,096,156 (1978)). The butyrolactone moieties are found in many natural products (Gunatilaka, A. A. L., Surendra, K. S. and Thomson, R. H., Phytochemistry, 23(4) 929–931 (1984) and Drioli, S., Felluga, F., Forzato, C., Nitti, P., Pitacco, G. and Valentin, E., J. Org. Chem., 63, 2385–2388 (1998)), insect pheromones (Naoshima, Y., Ozawa, H., Kondo, H. and Hayashi, S., Agric. Biol. Chem., 47(7) 1431–1434 (1983); Kim, C. S., Datta, P. K., Hara, T., Itoh, E. and Horiike, M., Bioscience Biotechnology and Biochemistry, 63(1) 152–154 (1999)), antifungal substances and flavor components (Shinohara, T. and Watanabe, M., J. Agri. Chem. Soc. Jap., 53 (7) 219–225 (1979) and Buttery, R. G. and Ling, L. C., J Agric Food Chem., 46(7) 2764–2769 (1998)) and also occur in the essential oil bearing plants.

Although several methods are available for the synthesis of simple γ-butyrolactone derivatives, however, synthesis of chiral centered biologically active γ-butyrolactone (Hullot, P., Cuvigny, T., Larcheveque, M. and Normant, H., Can. J. Chem., 55, 266–273 (1977); Tamaru, Y., Hojo, M. and Yoshida, Z., J. Org. Chem., 56, 1099–1105 (1991); Daugan, A. and Brown, E., J. Nat. Prod., 54(1) 110–118 (1991); Hartmann, B., Kanazama, A. M., Depres, J. P. and Greene, A. E., Tetrahedron Lett. 34(24) 3875–3876 (1993); Ishibashi, F.; Taniguchi, E., Phytochemistry, 49(2) 613–622 (1998) and Noyori, R., Kitamura, M., Ohkuma, T., Saya, N. and Kumobayashi, H., U.S. Pat. No. 5,420, 306 (1995)) and their analogues (Mangnus, E. M., Vliet, L. A. -van, Vandenput, D. A. L. and Zwanenburg, B., J. Agri. Food Chem., 40(7) 1222–1229 (1992); Belletire, J. L., Mahmoodi, N. O., J Nat. Prod., 55(2) 194–206 (1992) are tedious but even then the preparation of chiral γ-butyrolactones are the subject of many synthetic schemes (Carretero, J. C., Rojo, J., Tetrahedron Lett., 33, 7407–7410 (1992); Casey, M., Manage, A. C. and Murphy, P. J., Tetrahedron, 33, 965–968 (1992); Zschage, O. and Hoppe, D., Tetrahedron, 48, 5657–5666 (1992); Paulsen, H. and Hoppe, D., Tetrahedron, 48, 5667–5670 (1992); Chong, J. M. and Mar, E. K., Tetrahedron Lett., 31, 1981–1984 (1990) and Bachi, M. D. and Bosch, E. J., J. Org. Chem., 57, 4696–4705 (1992).

In particular, two chiral centered γ-butyrolactones having substituents such as an alkyl or alkenyl group are in more demand and they exist as either cis and/or trans isomer in nature (Bryan, V. and Chan, T. H., Tetrahedron Lett., 37(30), 5341–5342 (1996)). For example, whisky lactone, chemically known as 5-butyl-4-methyl-dihydro-2(3H)-furanone (also known as 3-methyl-4-octanolide or 4-hydroxy-3-methyloctanoic acid lactone) (1a) is a natural optically active disubstituted butyrolactone which is widely recognized and it has been identified as the most valuable additive responsible for the flavor of high quality whisky, wine, cognac and scotch etc (Nishimura, K. and Masuda, M., J. Food Sci. 36, 819 (1971); Kepner, R. E., Webb, A. D. and Muller, C. J., Am. J. Enol. Viticult, 23, 144 (1972); Etienne, M. and Manfred, S., Tetrahedron Lett., 25(40), 4491–4494 (1984) and Pérez-coello, M. S., Sánchez, M. A., García, E., González-viñas, M. A., Sanz, J. and Cabezudo, M. D., J. Agri. Food Chem., 48, 885–889 (2000)). Whisky lactone (1a) (also known as oak lactone or Querecus lactone) is a diastereomer of 3-methyl-4-octanolides (5-butyl-4-methyl-dihydro-2(3H)-furanone) which is found in whisky, wine, brandy and in extract of oak barrels. This lactone is important constituent of aging flavour and have so far been considered to be formed during aging from unknown precursors in wood barrels (Chem Abstr. 114, 181996v, 1991) which finally contributes to the flavour impact of the oak. The effect of oak barrels on the quality of wines are also influenced by several factors such as tree age, growth rate of tree and barrel size etc (Towey, J. P. and Waterhouse, A. L., Am. J. Enol. Viticult, 47(1), 17–20 (1996)).

In particular, the quality of the alcoholic beverages is affected largely by the presence of whisky lactone which is produced during the aging process. A wine aged for a longer period of time is realized to be of higher quality and is further influenced by several factors such as climatological conditions, fermentation, distillation, maturation and blending (Plaza, E. G., Munoz, R. G., Roca, J. M. L. and Martinez, A., J. Agric., Food Chem., 48, 736–741 (2000)). One of the isomers of this interesting whisky lactone (1a) is identified for the first time in whisky by Soumalainen and Nykanen in 1969 (Soumalainen, H. and Nykänen, L., Näbrungsmiddelindustrien, 23, 1–15 (1970), however, later on cis and trans isomers have been determined by several workers in matured cognac, Jamiaca rum and whiskies and found that the aroma threshold for the cis isomer is 92 ppb while for the trans-isomer is 460 ppb (Masuda, M. and Nishimura, K., Phytochemistry, 10, 1401–1402 (1971); Gunther, C. and Mosandl, A., Liebigs Ann. Chem. 2112–2122, (1986); Gunther, C. and Mosandl, A., Z. Lebensm. Unters. Forsch., 185, 1–4 (1987) and Maarse, H. and Berg F. V. D. In Understanding Natural flavours, edited by Piggott, J. R. and Paterson, A.; Blackie Academic & Professional, New York, pp. 243–267 (1994)). In fact, four stereoisomers of whisky lactone (1b) are known with the following taste and odor such as (3R, 4R)-5-butyl-4-methyl-dihydro-2(3H)-furanone with sweet, fresh, bright coconut smell (in 10% ethanol) and creamy, soft, coconut taste (10 ppm in aqueous saccharin); (3S, 4S)-5-butyl-4-methyl-dihydro-2(3H)-furanone with weak coconut note earthy, mouldy afterodor, hay note odor and herbaceous, reminiscent of coconut taste; (3S, 4R)-furanone derivative with spicy celery note, weak coconut, distinct green walnut note odor and sweet creamy fatty, reminiscent of coconut; (3R, 4S)-furanone derivative with intensive coconut note, afterodor, reminiscent of celery odor and weak spicy, herbaceous taste (Schreier, P., In: Bioflavour '87, Analysis. Biochemistry Biotechnology, Proceedings of the International Conference, Würzburg, Federal Republic of Germany, Sep. 29–30, 1987, Walter de Gruyter, New York, 55–74, (1988) and Eric, M., Raymond, B., Christine, L. G. and Jean-Louis, P., J. Agric.Food Chem., 48, 4306–4309, (2000)). A mixture of cis- and trans-whisky lactones also exhibits a repellent activity against mosquitoes and flies (Shono, Y. and Tsukasa, Y., Nippon Kokai Tokkyo Koho, 63-48203). However, considering all the above factors, it was realized that the productivity of oak lactone by aging whisky in oak barrel for several months/years in controlled temperature and other conditions is a laborious job, therefore, synthesis of whisky lactone (1a) has been developed by several chemists and some of the reported conventional methods include the following:

Typical prior art refrences include Masuda, M. and Nishimura, K., Chemistry Letters, 1333 (1981); Hoppe, D. and Bronneke, A., Tetrahedron Lett., 24, 1687 (1983)); Mori, M., Chuman, T. and Kato, K., Carbohydrate Research, 129, 73–86 (1984)); Frauenrath, H., Philipps, T., Liebigs Ann. Chem. 1951–1961 (1985)); Güenther, C. and Mosandl, A., Liebigs Ann. Chem., 2112–2121 (1986)); Sharma, G. V. M., Vepachedu, S. R. and Chandrasekhar, S., Synth. Commun. 20, 3403 (1990); Suzuki, Y., Mori, W., Ishizone, H., Naito, K. and Honda, T., Tetrahedron Lett. 33, 4931–4932 (1992) and Takashi, E., Hajime, M., Hiroshi, K. and Koshi, K., U.S. Pat. No. 5,216,177 (1993)).

It, therefore, becomes an object of the invention to eliminate the disadvantages existing with above known methods and others and to provide a rapid and economical method for the preparation of γ-butyrolactone of formula (1) as an analogue of whisky lactone (nicknamed as Querecus lactone or oak lactone) of formula (1a), via oxidation of dihydrotagetone (4) into 2,6-dimethyl-4-oxo-heptanoic acid (3) followed by reduction of 3 and lactonisation into γ-butyrolactone (1). In addition, γ-butyrolactone (1) with coconut flavour can also find application in flavouring the food stuffs since its analogue i.e.coconut aldehyde (γ-nonalactone, F.E.M.A. No. 2751) (1b) is responsible for flavouring a wide range of food stuffs including baked goods and confectionery.

OBJECTS OF THE INVENTION

The main object of the present invention is to provide a novel compound 5-isobutyl-3-methyl-4,5-dihydro-2(3H)-furanone of formula (1) as an analogue of whisky lactone or oak lactone or querecus lactone of formula (1a)

Yet another object of the invention is to provide a process for the preparation of compound 5-isobutyl-3-methyl-4,5-dihydro-2(3H)-furanone of formula (1) starting from dihydrotagetone of formula (4) which is, in fact, a natural acyclic monoterpene ketone (dihydrotagetone) found readily in *Tagetes* species.

Yet another object of the invention is to provide a simple process for industrial scale purification of starting material i.e. dihydrotagetone of the formula (4) from oil of *Tagetes* species.

Yet another object of the invention is to provide a simple process for proper utilization of dihydrotagetone of formula (4) into high valued products.

Yet another object of the invention is to provide a simple and efficient oxidizing reagent which utilizes the double bond of dihydrotagetone to generate a novel 2,6-dimethyl-4-oxo-heptanoic acid of formula (3) with one chiral center.

Yet another object of the invention is to provide a rapid method of converting dihydrotagetone of formula (4) into 2,6-dimethyl-4-oxo-heptanoic acid of formula (3) in microwave oven ranging from 5–30 minutes.

Yet another object of the invention is to accelerate oxidation of double bond of dihydrotagetone of formula (4) into 2,6-dimethyl-4-oxo-heptanoic acid of formula (3) by using alumina as a catalyst.

Yet another object of the invention is to provide a simple process for the preparation of 2,6-dimethyl-4-oxo-heptanoic acid of formula (3) in high yield for its use as a multipurpose additive in food and tobacco products since its analogue such as 2,6-dimethyl-5-oxo-heptanoic acid (found as a constituent of an important Italo-Mitcham peppermint oil i.e. *Menthaxpiperita L.*) is well known for its wide application in perfumery, flavour and pharmaceutical industry.

Yet another object of the invention is to convert 2,6-dimethyl-4-oxo-heptanoic acid of formula (3) into corresponding 4-hydroxy acid or 4-oxo ester or the like.

Yet another object of the invention is to provide an industrial method for the preparation of 5-isobutyl-3-methyl-4,5-dihydro-2(3H)-furanone of formula (1) in high yield and purity via reduction of above obtained 2,6- dimethyl-4-oxo-heptanoic acid of formula (3) with metal hydride followed by lactonisation into 5-isobutyl-3-methyl-4,5-dihydro-2(3H)-furanone of formula (1).

Yet another object of the present invention is to introduce two chiral centred 5-isobutyl-3-methyl-4,5-dihydro-2(3H)-furanone of formula (1) since it is well established that chiral discrimination is an important principal of odor perception.

Yet another object of the invention is to provide 5-isobutyl-3-methyl-4,5-dihydro-2(3H)-furanone of formula (1) as a new product for the first time for its wide application in flavours, perfumery, cosmetics, soft and alcoholic beverages and pharmaceutical industries for its biological activities.

Yet another object of the invention is to provide coconut flavoured 5-isobutyl-3-methyl-4,5-dihydro-2(3H)-furanone of formula (1) for its use as a substitute of several other coconut flavouring γ-butyrolactones for its application in food and beverage or the like.

Yet another object of the invention is to provide as an analogue of coconut aldehyde (aldehyde C-18) of formula (1b) which is one of the most frequently used lactones in perfumery and flavour industries (F.E.M.A. No. 2781).

SUMMARY OF THE INVENTION

The present invention provides a method for preparing 3,5-disubstituted γ-butyrolactone, via which two chiral centered lactone of formula (1) with coconut flavour, an analogue of natural whisky lactone (also named as Quercus lactone or oak lactone) of formula (1a) responsible for high quality of whisky, wine, brandy and scotch is formed by utilizing a natural inexpensive acyclic monoterpene ketone (dihydrotagetone) of formula (4), isolated from the oil of *Tagetes* sp., which was smoothly oxidized with meta-periodate/potassium permanganate into 2,6-dimethyl-4-oxo-heptanoic acid of formula (3). The reduction of oxo acid (3) with sodium borohydride followed by lactonisation in acidic medium furnished a new two chiral centered 5-isobutyl-3-methyl-4,5-dihydro-2(3H)-furanone of formula (1) which has wide applications in flavouring food stuffs, soft and alcoholic beverages, perfumery and pharmaceutical industries.

The present invention also relates to 2,6-dimethyl-4-oxo-heptanoic acid of formula (3) not only as a precursor for the synthesis of whisky lactone of formula (1a) but also as a novel analogue of 2,6-dimethyl-5-oxo-heptanoic acid (a constituent of well known essential oil of *Mentha×piperita*) which has wide applications in flavouring food stuffs, soft and alcoholic beverages, perfumery and pharmaceutical industries.

BRIEF DESCRIPTION OF THE ACCOMPANYING DRAWING

Figure 1:
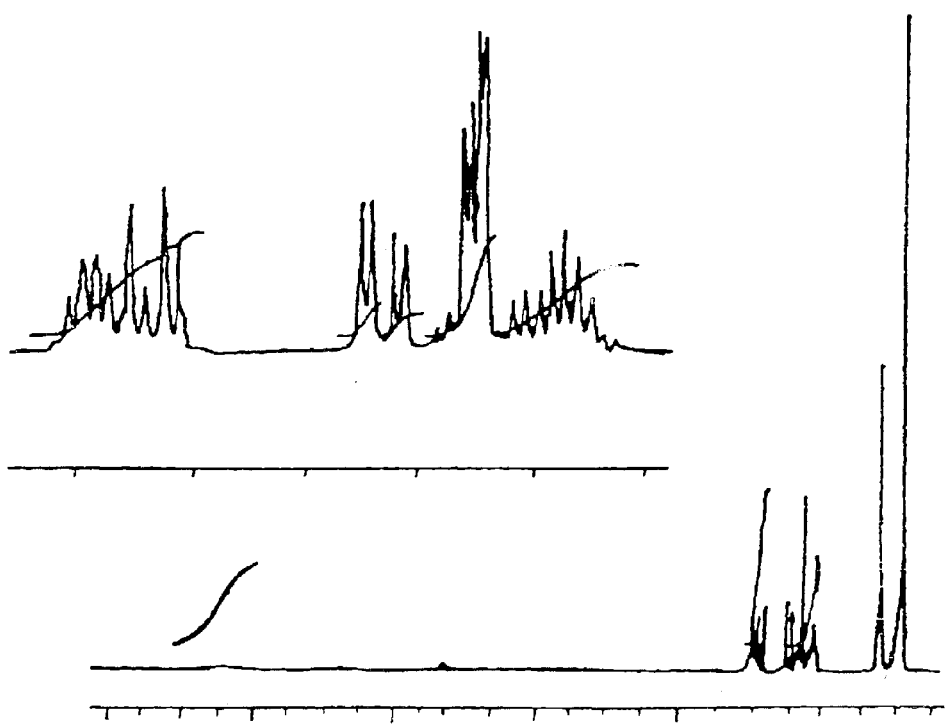
FIG. 1 is $^1$H NMR (300 MHz) spectra of 2,6-dimethyl-4-oxo-heptanoic acid (in CDCl$_3$) of the reaction product of Example I containing the compound having the structure: ##STR1##.

Accordingly, the present invention provides "a novel method for converting dihydrotagetone into coconut flavoured 5-isobutyl-3-methyl-4,5-dihydro-2(3H)-furanone with two chiral centers: an analogue of natural whisky lactone and coconut aldehyde" of the general formula (1),

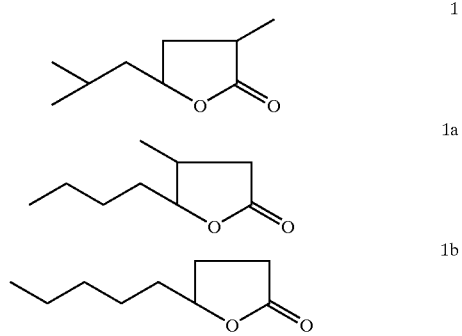

the said method comprising
a. adsorbing *Tagetes minuta* oil on an adsorbent selected from but not limited to alumina and silica gel;
b. loading adsorbent obtained from step (a) on a soxhlet extractor and washing with a non polar solvent (cold percolation) selected from but not limited to petroleum ether and hexane for removing the non polar constituents;
c. isolating the dihydrotagetone rich fractions using hot hexane percolation with increasing percentage of ethylacetate starting from 0.2 upto 5%;
d. concentrating the above separated fractions under reduced pressure to obtain a dihydrotagetone rich concentrate;
e. loading above concentrate on alumina or silica gel column and eluting the column with a non polar solvent selected from but not limited to hexane and petroleum ether;
f. eluting the column further with increasing percentage of ethyl acetate upto 5% in hexane;
g. concentrating the resulting hexane-ethylacetate fractions under reduced pressure to obtain dihydrotagetone of formula (4) in 99% or more purity;
h. providing dihydrotagetone of formula (4) in organic solvent selected from the group consisting of ether selected from but not limited to tetrahydrofuran, dimethoxyethane and dioxane, alcohol selected from but not limited to butanol and t-butyl alcohol, ketone selected from but not limited to acetone and methyl ethyl ketone;
i. oxidising dihydrotagetone of formula (4) in the presence of an oxidizing reagent selected from but not limited to sodium meta-periodate, potassium meta-periodate and ruthenium tertaoxide in the range of 2 to 8 times mole of dihydrotagetone of formula (4) and a co-oxidizing agent selected from but not limited to potassium permanganate and sodium permanganate in the range of 0.1 to 0.6 times mole of dihydrotagetone (starting material) of formula (4);
j. adding a base selected from the group consisting of but not limited to sodium carbonate, sodium bicarbonate, potassium carbonate, lithium carbonate and sodium hydroxide in the range of 1 to 4 times mole of dihydrotagetone of formula (4) to the above said solution obtained in step (i);

k. maintaining the temperature between −15° C. to +90° C. during oxidation steps from (h) to (j) for a period ranging from 4–48 hours;

l. destroying the excess permanganate from the above reaction mixture with saturated solution of sodium bisulphite or sodium metabisulphite;

m. filtering the above reaction mixture, washing, acidifying, and removing the solvent under reduced pressure, followed by extraction and chromatography to obtain 2,6-dimethyl-4-oxo-heptanoic acid of formula (3) with 68% yield or more;

n. providing 4-oxo acid of formula (3) under stirring in a solvent selected from the group consisting of ether but not limited to tetrahydrofuran, dimethoxyetane and dioxane, alcohol but not limited to methanol, butanol and t-butyl alcohol, chlorinated solvent but not limited to dichloromethane and chloroform;

o. adding a base selected from the group consisting of but not limited to sodium bicarbonate or sodium hydroxide or potassium carbonate to the resultant solution to make salt of the oxy acid of formula (3);

p. reducing salt of oxo acid of formula (3) to hydroxy acid of formula (2) in the presence of a reducing agent selected from but not limited to sodium borohydride or lithium aluminum hydride in the range of 0.5–3 times mole at a reaction temperature varying from −15 to 50° C.;

q. removing the organic solvent under vacuum and acidifying the cooled aqueous alcoholic solution at −10° C. to 0° C. with an acid selected from the group but not limited to hydrochloric acid, sulfuric acid, acetic acid, acetic anhydride for a period ranging between 30 minutes to 8 hours and finally isolating the product 5-isobutyl-3-methyl-4,5-dihydro-2(3H)-furanone also known as 4-isobutyl-2-methyl-4-butanolide) of formula (1) in 76% or more yield by extraction and chromatography in usual manner.

In an embodiment of the present invention soxhlet extractor using cold hexane percolation removes ocimene, one of the main and unwanted constituent, from tagetes oil.

In an embodiment of the present invention soxhlet extraction of alumina or silica gel bound tagetes oil with hot percolation of non polar solvent removes polymerized material efficiently since it remains stuck on alumina or silica.

In an embodiment of the present invention a simple process is employed for the industrial scale purification of dihydrotagetone of formula (4) from oil of *Tagetes* species.

In an embodiment of the present invention a simple process is employed for the proper utilization of dihydrotagetone of formula (4) into high valued products.

In an embodiment of the present invention said process is capable of preparing 2,6-dimethyl-4-oxo-heptanoic acid of formula (3) on commercial scale.

In an embodiment of the present invention 2,6-dimethyl-4-oxo-heptanoic acid of formula (3) has acidic sweet aroma.

In an embodiment of the present invention compound 2,6-dimethyl-4-oxo-heptanoic acid of formula (3) has bifunctionality which is capable of converting compound 3 into several value added products.

In an embodiment of the present invention an alternative process is employed for the rapid conversion of dihydrotagetone of formula (4) into 2,6-dimethyl-4-oxo-heptanoic acid (3) in microwave oven ranging from 5–30 minutes where the rate of reaction is further accelerated by adding alumina.

In an embodiment of the present invention is to provide a simple process for preparation of 2,6-dimethyl-4-oxo-heptanoic acid of formula (3) as an analogue of 2,6-dimethyl-5-oxo-heptanoic acid which is found as a constituent of an important Italo-Mitcham peppermint oil i.e. *Mentha x piperita L.* and well known for its wide application in perfumery, flavour and pharmaceutical industry.

In an embodiment of the present invention 2,6-dimethyl-4-oxo-heptanoic acid of formula (3) is a novel compound and useful as a chiral synthone for its application in asymmetric chemistry.

In an embodiment of the present invention compound 2,6-dimethyl-4-oxo-heptanoic acid of formula (3) is useful as a versatile intermediate for converting it into corresponding 4-oxo ester, 4-hydroxy ester and 4-hydroxy acid for various formulations in flavour, perfumery and pharmaceutical industries.

In an embodiment of the present invention compound 2,6-dimethyl-4-oxo-heptanoic acid of formula (3) is useful for various formulations in flavouring food stuffs, soft and alcoholic beverages, herbal and tobacco products, perfumery and pharmaceutical aids in desired and acceptable amount varying from ppm to mg based on the type of products.

In an embodiment of the present invention a simple process is employed for the preparation for novel 5-isobutyl-3-methyl-4,5-dihydro-2(3H)-furanone of formula (1) in high yield and high purity.

In an embodiment of the present invention a simple process is employed for the preparation of novel 5-isobutyl-3-methyl-4,5-dihydro-2(3H)-furanone of formula (1) as an analogue of whisky lactone or oak lactone or quercus lactone.

In an embodiment of the present invention compound 5-isobutyl-3-methyl-4,5-dihydro-2(3H)-furanone of formula (1) is capable of providing aroma of whisky lactone to high quality alcoholic beverages which generally comes after aging wine, brandy scotch and whisky in a specific oak barren for several months/years, however, this invention removes all the hastle.

In an embodiment of the present invention compound 5-isobutyl-3-methyl-4,5-dihydro-2(3H)-furanone of formula (1) is capable of undergoing conversion into several value added products including furans and pyrrolidones etc.

In an embodiment of the present invention compound 5-isobutyl-3-methyl-4,5-dihydro-2(3H)-furanone of formula (1) is a stable compound.

In an embodiment of the present invention compound 5-isobutyl-3-methyl-4,5-dihydro-2(3H)-furanone of formula (1) has coconut like aroma.

In an embodiment of the present invention 5-isobutyl-3-methyl-4,5-dihydro-2(3H)-furanone of formula (1) as an analogue of whisky lactone (1a) is useful in formulation of high quality alcoholic beverages including wine, brandy scotch and whisky.

In an embodiment of the present invention coconut aroma of 5-isobutyl-3-methyl-4,5-dihydro-2(3H)-furanone of formula (1) is useful as multipurposes additive for various formulations in flavouring food stuffs, soft and alcoholic beverages, herbal and tobacco products, perfumery and pharmaceutical aids in desired and acceptable amount varying from ppm to mg based on the type of products.

In an embodiment of the present invention a simple process is employed for the preparation of novel 5-isobutyl-3-methyl-4,5-dihydro-2(3H)-furanone of formula (1) since an analogue of coconut aldehyde (commonly known as γ-nonalactone) (1b) is one of the most frequently used lactones in perfumery and flavour industries (F.E.M.A. No. 2781).

DETAILED DESCRIPTION OF THE INVENTION

Alcoholic beverages contain various kinds of flavour compounds with flavour ranging from strong to mild (Schreier, P., CRC Food Sci. Nut., 12, 59–111, (1979)). In particular, the quality of the alcoholic beverages is affected largely by the source of material, enzymatic action, process, storage, transportation and aging process (Simpson, R., Vitis, 17, 274–287 (1978) and Maga, J. A., Food Rev. Intern., 5, 39–99, (1989)). Aging techniques are widely used to produce wine, whisky, miso and fermented foods and special aging methods are devised for each product (Paterson, A. and Piggott, J. R., In: The Distilled Beverage Flavour, recent Developments, Ellis Horwood, Chichester, 151–169 (1989)). Oak barrels have been used to store and age wine and other beverages for centuries for enhancing the flavour of the beverage by incorporating flavour components from oak into the beverages in which cis-oak lactone has superior scent than trans-isomer (Otsuka, K., Zenibayashi, Y., Itoh, M. and Totsuka, A., Agric. Biol. Chem., 38, 485, (1974)). White oak obtained from United States and France is of highest quality as these barrels do not leak and finally produce high quality wines including sherries as well as distilled spirits—principally whiskies, bourbon and scotch although other countries do produce some oak barrels too. Some commercial oak species found in France and across Europe are *Quercus pedunculata* (*Q. robur*), *Q. sessilis* (*Q. petraea* or *Q. sessiliflora*) while *Q. alba, Q. garryana* are found through out United States (Alamo, M. D., Bemal, J. L. and Cordovés, C. G., J. Agric. Food Chem., 48, 4613–4618 (2600)). However oak lactone (whisky lactone) is found in traces in plant kingdom and for these reasons several methods of preparation of whisky lactone have been reported and some of the important methods are:

1) 1,4-addition of lithium dimethylcuprate to the butenolide derivative, but this is not a convenient synthesis (Vigneron, J. P., Meric, R. and Dhaenens, M., Tetrahedron Lett., 21, 2057 (1980))as it requires expensive reagents.

2) A method utilizing substituted carboxylic acid and butylene oxide derivatives as a starting material, however, this method requires highly flammable lithium metal to complete the series of reaction, therefore, not applicable on an industrial scale. Moreover, the starting materials i.e acid and oxide derivatives need to be synthesized in several steps (Moret, E. and Schlosser, M., in Tetrahedron Lett., 25: 4491–4494, (1984) and Fujita, T., Watanabe, S. and Suga, K. in Aust. J. Chem., 27: 2205–2208, (1971)).

3) A method using acyclic vinyl sulphoxide as a starting material involves many steps and several expensive reagent combinations (Marino, J. P. and Pradilla de la, R. F., Tetrahedron Letters, 26(44), 5381–5384 (1985)).

4) A method utilizing ribonolactone as a starting material, however, ribonolactone is expensive and the reaction steps are complicated (Ortuno, R. M., Merce, R. and Font, J., Tertahedron, 43,4497–4506 (1987)).

5) A method utilizing optically active lactone as a starting material, however, lactone is expensive and the reaction steps are complicated (Bloch, R. and Gilbert, L., J. Org. Chem. 52, 4603–4605 (1987).

6) A method utilizing 2-butenyl carbamate as a starting material, however, this method requires the use of specific reagent such as (−) sparteine but even then the optical purity of lactone derivative obtained is not sufficiently high (Hoppe, D. and Zschage, O., Angew. Chem. Int. Ed. Engl., 28, 69–71 (1989)).

7) A method using chiral methyl-β-formylcarboxylates derivative as a starting material involves many steps and several expensive reagent combinations (Thomas, K., Agnes, J. and Hans, U. R., Chem. Ber., 122, 2165–2175 (1989)).

8) A method using cyclopentane derivative as a starting material involves many steps and several expensive reagent combinations (Suzuki, Y., Wakako, M., Hiroyuki, I., Koichi, N. and Toshio, H., Tetrahedron Letters, 33(34), 4931–4932 (1992)).

9) A method using a naturally occurring geraniol as a starting material involves many steps and several expensive reagent combinations (Taber, D. F. and Jonathan, B. H., J. Org. Chem., 59, 4004–4006 (1994).

10) A method using levoglucosenone is made to react with methyl lithium in the presence of copper iodide in order to introduce a methyl group into an enone group of levoglucosenone and to obtain 1,6-anhydro-3,4-dideoxy-4-C-methyl-beta-D-erythro-hexopyranose-2-ulose. This methyl compound is oxidized in acetic acid for lactone formation and (3S, 4S)-5-hydroxy-3-methylpentan-4-olide is thus obtained. Further, this lactone is made to react with tosyl chloride in anhydrous pyridine to obtain (3S, 4S)-3-methyl-5-tosyloxypentan-4-olide (tosylate). The obtained tosylate is alkylated with n-propyl lithium in the presence of copper iodide to obtain (3S, 4R)-3-methyl-4-octanolide. Here, the (3S, 4S)-3-methyl-5-tosyloxypentan-4-olide may be treated with potassium carbonate to cleave lactone once, thereby obtaining epoxide. After that, the obtained epoxide is alkylated to form lactone ring again to obtain (3S, 4R)-3-methyl-4-octanolide (whisky lactone) (1a), however, this method has various limitations and can not be upscaled on industrial basis ((Takashi, E., Katsuya, M., Hajime, Y., Koshi, K., Hiroshi, K. and Hajime, M., Heterocycles, 31(9), 1585–1588 (1990)and Takashi, E., Hajime, M., Hiroshi, K. and Koshi, K., U.S. Pat. No. 5,216,177 (1993)).

All the above methods including patent have various limitations and none of them have been found suitable for the economical production of whisky lactone (4-butyl-3-methyl-butyrolactone) (1a) and therefore, it was realized that any synthetic analogue of (4-isobutyl-2-methyl-butyrolactone or 5-sec-butyl-3-methyl-4,5-dihydro-2(3H)-furanone) (1) that can be prepared more readily. In seeking a simple synthesis of (1) from a cheaper material and reagents, dihydrotagetone (4) (isolated from Tagetes oil) ((Lawrence, B. M., Powell, R. H., Smith T. W. and Kramer, S., Perfumer and Flavorist, 10(6), 56–58 (1985)) appears as a simple and economical starting material in which dihydrotagetone undergoes oxidation and reduction followed by lactonization to afford γ-butyrolactone (1) which, in fact, would offer the advantages of simplicity and directness and can be applied for large scale preparations. In addition, this new butyrolactone (1) may have better applications than whisky lactone (1a) since in many cases the structural modifications towards analogue formations are proved to be more biologically active and useful than parent compounds (William, D. K., Jeffrey, C. B., Dalia, R. J., Kenneth, G. H., Sidney, M. H., Gregory, G., Mary, J. C., Francis, L. M., Leo, F. F., Randall. K. J. and Robert, P. H., J. Med. Chem., 34, 98–107 (1991); Xuechao, W., Yuxin, C., Xinfu, P. and Yaozu, C., J. Indian Chem. Soc., 73, 217–219 (1996); Vivek, K., Thomas, F. M. and Jane, V. A., J. Med. Chem. 43, 5050–5054 (2000) e.g a δ-nonalactone (mol. formula= $C_9H_{16}O_2$, six membered lactone), an isomer of the well known γ-nonalactone (mol. formula =$C_9H_{16}O_2$, five membered lactone) (1b) is commercially available and having extensive use in perfumery compositions as a modifier for coconut aldehyde (Flavour and Extract Manufactures Association, F.E.M.A. No. 2781) (1a) (Steffen, A., In: Perfume and Flavor Chemicals, Part II, Allured Publishing Corporation, Carol Stream, Ill. 60188-2787, (1994)).

Dihydrotagetone (2,7-dimethyl-oct-1-en-5-none or 2,6-dimethyloct-7-en-4-one) (4), a natural acyclic monoterpene ketone, which is used in the present invention can be easily isolated from several plants such as *Tagetes* spp. (Baser, K H. C. and Malyer, H., J Essential Oil Research, 8(3), 337–338 (1996)) and *Ocimum basilicum* var. *hispidum* (Ruberto, G., Spadaro, A., Piattelli, M., Piozzi, F. and Passannanti, S., Flavour and Fragrance J. 6(3), 225–227 (1991) or can be synthesized by the reported methods (Jones, T. G. H. and Smith, F. B., J. Chem. Soc., 127, 2530 (1925); Vig, O. P., Matta, K. L. and Raj, I., J. Indian Chem. Soc., 41, 752 (1964); Vig, O. P., Matta, K. L., Bhatia, M. S. and Anand, R. C., Indian J. Chem, 8, 107 (1970); McAndrew, B. A. and Riezebos, G., J. Chem. Soc. Perkin Trans I, 367–369 (1972) and Le Borgne, J. F.; Larcheveque, T. M. and Normant, H., Tetrahedron Letters 17, 1379–1380 (1976)). *Tagetes* spp. include *Tagets signata* [*tenuifolia*] B. (Bodrug, M. V., Dragalin, I. P. and Vlad, P. F., Rastitel'nye Resursy 19(3), 323–327 (1983) and Hethelyi, E., Danos, B., Tetenyi, P. and Koczka, I., Flavour and Fragrance J. 1(4–5), 169–173 (1986)) and *Tagetes riojana F.* (Zygadlo J. A., J. of Essential Oil Research 7(3), 319–320 (1995)), *Tagetes argentina C.* (Zygadlo, J. A., Maestri, D. M. and Espinar, L. A., J. of Essential Oil Research 5(1), 85–86 (1993) and J. of Essential Oil Research 7(1), 111–112 (1995), *Tagetes lemmonii G.* (Tucker, A. O. and Maciarello, M. J. J. of Essential Oil Research 8(4), 417–418 (1996) and *Tagetes minuta* (commonly known as "marigold").

*Tagetes minuta* (family: Asteracea) is most suitable essential oil bearing plant and therefore, cultivated in several countries such as Egypt, France, Morocco, Brazil, United States and India for its applications in perfumary, flavour and pharmaceutical industries (Chalchat, J. C., Garry, R. P. and Muhayimana, A., J. Essential Oil Research, & (4), 375–386 (1995)). Out of one hundred and four components, the major constituents of the essential oil of *T. minuta* are tagetone, E/Z-ocimenone, E/Z-ocimene, germacrene, limonene, trans-anethole and desired dihydrotegetone (Hethelyi, E., Danos, B. Tetenyi, P. and Koczka, I., Flavour and Fragrance J., 1(4–5), 169–173 (1986); Wilson, R. A., zampino, M. J., Mookherjee, B. D., ouwerkerk, A. and Monteleone, M. G., U.S. Pat. No. 4,960,754 (1990). Tagetes oil has been known from long due to its pleasant and powerful odors and flavours, however, tagetes oil does not have very attractive price in market and also has storage problem as it constituents undergo polymerization such as the highly conjugated tagetone, ocimenone and ocimene etc. Polymerization deteriorates the quality of the tagetes oil as well as makes it unsuitable for any kind of applications, therefore, an economic temptation arose to utilize this acyclic monoterpene ketone (dihydrotagetone) (4) for its conversion into high valued products which appeared to us γ-butyrolactone (1). Among the *Tagetes* spp., the chemical composition of *T. minuta* oil is well documented with the seasonal variation and the percentage of dihydrotagetone is detected upto 60% or more (Singh, B., Sood, R. P., Singh, V., J. Essential Oil Research, 4(5), 525–526 (1992); Thappa, R. K., Agarwal, S. G., Kalia, N. K., Ramesh, K. and Kapoor, R., J. Essential Oil Research, 5(4), 375–379 (1993); Singh, B. and Sood, R. P., Indian Perfumer, 39, 102–106 (1995); Chisowa, E. H., Hall, D. R. and Farman, D. I., J. Essential Oil Research, 10(2), 183–184 (1998); Garg, S. N. and Mehta, V. D., Phytochemistry, 48(2), 395–396 (1998); Rao, E. V. S. P., Syamasundar, K. V., Gopinath, C. T., Ramesh, S. and Prakasarao, E. V. S., J. Essential oil Research, 11(2), 259–261 (1999)).

As dihydrotagete (4) is a starting material, therefore it becomes very important to develop a simple and economical process for the separation of dihydrotegetone from the mixtures of closely related several constituents (tagetone, ocimenone etc) of *Tagetes minuta* oil which is done by two step process i.e Soxhlet extraction of tagetes oil adsorbed on solid support followed by column chromatography. Soxhlet extraction of solid (taken in thimble) occupies an important place amongst the technologies for separation of the desired constituents from its various constituents. However the adsorbance of tagetes oil on solid support such as silica gel, alumina or celite and Soxhlet extraction with non polar solvents such as petroleum ether and hexane was found extremely successful to separate dihydrotegetone from remaining constituents since more polar constituents and polymerized materials bound on solid supports does not move with non polar solvents. It is worthwhile to mention that initial cold perculation of alumina bound tagetes oil using hexane allows removal of non polar constituents mainly ocimene, however, warm percolation (with hexane) of Soxhlet extractor brings down yellow coloured dihydrotagetone rich fractions. The fractions were monitored on TLC plate and the desired fractions were combined and solvent was removed under vacuum to afford yellow liquid. The yellow liquid was further loaded on silica gel column and eluted with hexane with an increasing amount of ethyl acetate (upto 5%) afforded dihydrotagetone as a sweet smelling liquid in above 99% purity by gas chromatography (tr=16.25 min) (performed on a Shimadzu-GC-14B/C-R7A gas chromatograph with the following conditions: carbovax column; 0.25 mm/60 m; injector 250° C.; FID detector 230° C.; temp. programme 40 (hold for 2 min.) to 190° C. (hold for 20 min.) 5° C. min$^{-1}$). In this two step purification, Soxhlet extraction is found very efficient to take out dihydrotagetone even from polymerized tagetes oil since dihydrotagetone does not polymerize and its percentage found to be higher in old polymerized oil. Therefore, above developed Soxhlet extraction appears as an effective process otherwise purification of tagetes oil directly on column chromatography is tedious and time consuming and does not allow to obtain dihydrotagetone in high purity. On the basis of IR and NMR spectrum of liquid (4) and its comparison with those reported in the literature, the liquid was confirmed to be dihydrotagetone (4). This by-functional alkenone (4) appears as an attractive intermediate in which without protecting ketone function, it is possible to change the terminal double bond into corresponding acid with Lemieux-von Rudloff reagent (Lemieux, R. U., vonRudloff, E., Can. J. Chem., 33, 1701 (1995)).

Oxidation of an alkene (Alan, H. H., In: Methods for the Oxidation of Organic Compounds, Academic Press Inc., New York, 71–152 (1985)) with periodate/permagnate (vonrudloff, E., Can. J. Chem., 43, 1784 (1965) or ruthenium tetraoxide/periodate (Pappo, R. and Becker, A., Bull. Res. Counc., Isr., Sect., A5A, 300 (1956) and Webster, F. X., Enterrios, J. J. and Silverstein, R. M., J. Org. Chem., 52, 689–691 (1987)) cleaves the carbon-carbon double bond to give ketone and/or carboxyclic acid depending upon the substituted alkene, however, treatment of dihydrotagetone with aqueous solution containing an excess of periodate and a catalytic amount of potassium permanganate afforded corresponding oxo acid in 71% yield ( by conventional method). The structure of this oxo acid was determined by their spectral data (Example 2) and assigned as a 2,6-dimethyl-4-oxo-heptanoic acid (mol. formula=$C_9H_{16}O_3$) (3) with one chiral center as a new product which finally appeared as an anologue of 2,6-dimethyl-5-oxo-heptanoic acid (mol. formula=$C_9H_{16}O_3$) present in well known essential oil of *Mentha x piperita L.* (Italo-Mitcham peppermint oil) (Nishimura, O. and Mihara, S., Flavors and Fragrances, Aworld Perspective, Proceeding 10 th Internatinal Congress of Essential oils, Washington, D.C., 1986, ed. Lawrence, B. M., Mookherjee, B. D. and Eastman, R. H., Elsevier, Amsterdam, 375 (1988) and Regula, N., Alain, V., Flavour Fragrance J., 13, 203–208 (1998)). The olfactory assessment of this interesting oxo acid (3) is performed as per Indian standard of 2284, 1997 (Bureau of Indian Standard, Manak Bhavan, 9 Bahadur Shah Zafar Marg, New Delhi). The odour effect of oxo acid (3) perceived by the olfactory nerves on smelling a strip impregnated with an oil is giving the impression of sweetness with the acidity thereby enabling its use as multipurpose additives in the areas of soft drinks, desserts and tobacco products etc since several related 4-oxoacid derivatives such as 4-oxovaleric acid and volatile acidic fraction of sun-cured *Nicotiana tabacum* (Greek tobacco) (Kimland, B., Aasen, A. J., Almqvist, S. O., Aroino, P. and Enzeil, C. R., Phytochemistry 12:835–847 (1973)) are well known for their wide applications in flavour industries especially as tobacco additives to improve the tobacco flavour. In addition, 2,6-dimethyl-4-oxo-heptanoic acid (3) can also be converted into corresponding 4-oxoesters and 4-hydroxyacids which are found in plant kingdom and are widely used in flavour industries (Taylor, A. J. and Mottram, D. S., In: Flavour Science, Recent Developments, The Royal Society of Chemistry, Cambridge CB4 4WF, U.K., 151–162 (1996)). However, keeping in view all the informations collected from literature, 2,6-dimethyl-4-oxo-heptanoic acid (3) appears itself an interesting product having a wide scope for vigorous biological activities as well as new additive for various applications particularly in flavour industries. With the world market project expansion towards natural flavours, there is clearly a huge potential for the application of new and simple techniques for production in which microwave assisted (Bose, A. K., Banik, B. K., Lavlinskaia, N., Jayaraman, M. and Manhas, M. S. Chemtech, 27, 18, (1997)) oxidation of dihydrotagetone (conducted for the first time) appeared as a rapid, economical and high yielding method for production of 4-oxo acid (3) (81% yield) higher than the above conventional method (71% yield). It is worthwhile to mention that the addition of alumina during microwave oxidation of dihydrotagetone provide not only a solid support (McKillop, A., Young, D. W., Synthesis, 481–500 (1979) and Clark, J. H., Gullen, S. R., Barlow, S. J. and Bastock, T. W. J. Chem. Soc. Perkin Trans 2, 1117, (1994)) but it also accelerates the oxidation reaction (Example II).

Figure 4:
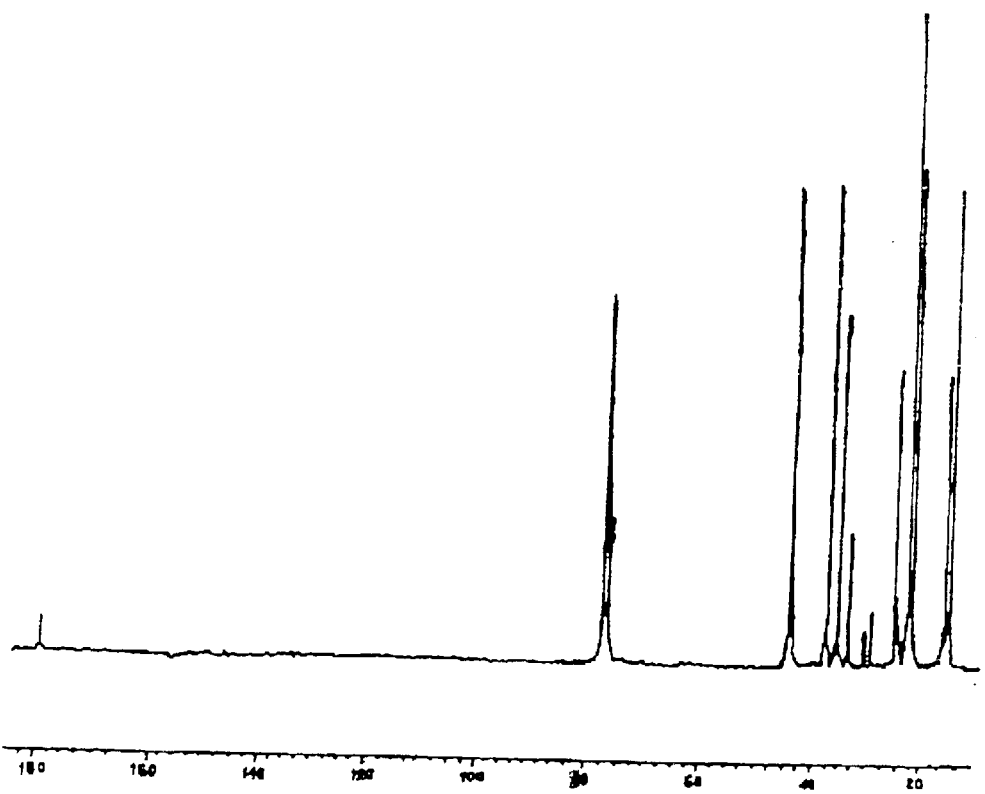
FIG. 4 is $^{13}$C NMR (75.4 MHz) spectra of 5-isobutyl-3-methyl-4,5-dihydro-2(3H)-furanone (in CDCl$_3$) of the reaction product of Example II containing the compound having the structure: ##STR2##.
Figure 5:
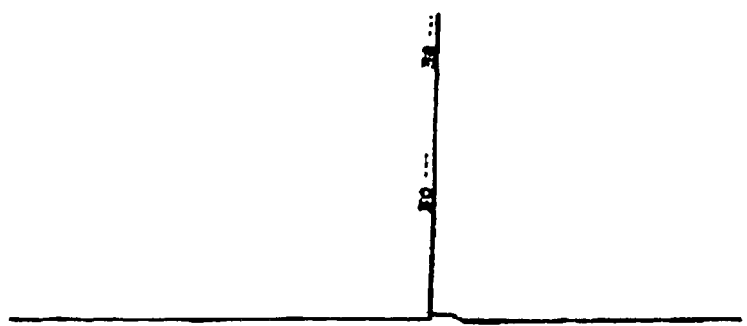
FIG. 5 is the GC of 5-isobutyl-3-methyl-4,5-dihydro-2(3H)-furanone of the reaction product of Example II containing the compound having the structure: ##STR2##.

Reduction of this 4-keto acid (3) with metal hydride such as sodium borohydride, lithium aluminium hydride furnished hydroxy acid (2) (without isolation) which when treated directly with strong acid such as hydrochloric acid, sulphuric acid, paratoluene sulphonic acid, acetic anhydride, trifluro acetic acid or the like gave coconut flavoured γ-butyrolactone (1) as diastereoisomeric mixture (68:32) on the basis of NMR (Example III and FIG. 4) and GC (FIG. 5).

This semisynthetic butyrolactone (1) is as good as the natural whisky lactone (1a) and has added advantage that it can be made available in any quantity required utilizing cheaper starting material and inexpensive reagents and also in less time with overall good yield. In addition, this coconut flavoured γ-butyrolactone (1) appears as a multipurpose additive for flavouring a variety of food products of coconut flavour. Scanning of literature reveals that there are some lactones such as 3-methyl-n-γ-lactone (F.E.M.A. 3103) and γ-nonyllactone (coconut aldehyde) (F.E.M.A. 2781) or the like which have aroma like coconut and the Flavour and Extract Manufacturers Association (F.E.M.A.) monograph cites their uses in a wide range of food stuffs including baked goods and confectionery (Steffen, A., In: Perfume and Flavor Chemicals, Part I & II, Allured Publishing Corporation, Carol Stream, Ill. 60188-2787, (1994)). The above coconut aldehyde (also known as γ-nonyllactone or 4-hydroxynonanoic acid, lactone or prunolide or γ-nonalactone or γ-n-amyl butyrolactone or abricolin or aldehyde C-18) (F.E.M.A. 2781) is one of the most frequently used lactones in perfumes and flavours and its field of application reaches from the finest luxury perfumes to inexpensive masking odours, from gardenia flowers bases to coconut candy flavours. Its creamy, coconutty, delicately fruity (in extreme dilution) and floral-musky odour of excellent tenacity is often utilized along with that of undecanolide (so-called aldehyde C-14) in garden, tuberose, honeysuckle, stephanotis, plumeria, jasmine and many other heavy floral types. In flavours, the coconut aldehyde finds even more extensive use, and often in much higher concentration. Besides coconut, this material is used in imitation of bitter-almond, in fruit blends (fixative), berry complexes, nut variations, American cherry flavour etc. in which concentration may vary from 10 to 50 ppm in the finished product (G.R.A.S, F.E.M.A. No. 2781). This important coconut aldehyde can be prepared by either from methylacrylate plus hexanol with di-tertiary-butylperoxide or from undecylenic acid with malonic acid condensation or from nonenoic acid (obtained from castor oil) by lactonization. The importance of coconut flavour can also be understood as a combination of diluted coconut water concentrate with equal amount of milk, water and sugar give a delicious drink. Recently, coconut water concentrate is developed by Miracle Food Processors International Ltd. (MFPIL) and the quality was certified by Central Food Technology Research Institute (CFTRI), Mysore (India) and at a research center KIN in Germany. Considering all the above factors, it appeared to us that our new γ-butyrolactone (1) with coconut flavour is not only an analogue of whisky lactone (1a) but can also be used as a substitute to coconut aldehyde or aldehyde C-18 (1b) which occurs in peaches, apricots and coconut (Bennett, H., In: Concise Chemical and Technical Dictionary, Fourth Edition, ed., Edward, A., Publishing Ltd., 41 Bedford Square London, WC1B, 3DQ, 48, (1986) and Orlindo, S. In: Handbook of Perfumes and Flavours, Chemical Publishing Co., Inc., New York, N.Y. 152 (1990)).

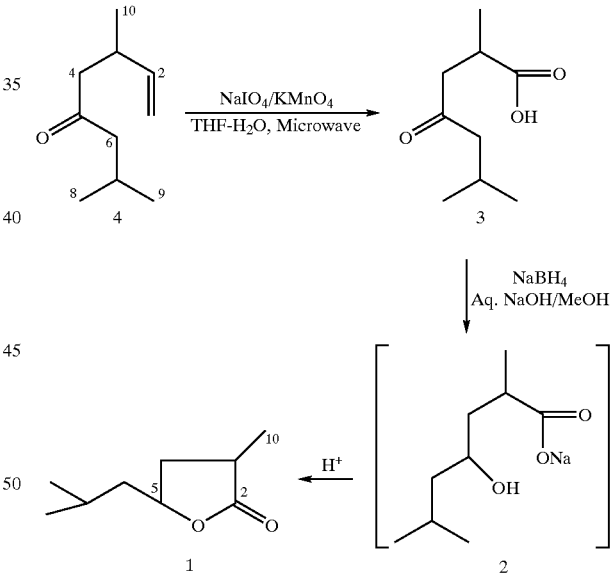

EXAMPLES

The following examples are given by way of illustration of the present invention and should not be considered to limit the scope of the present invention.

Example I (a) Isolation of dihydrotagetone(4) from *Tagetes minuta* oil: The large scale purification of *tagetes* oil is achieved by adsorbing it on alumina (6–10 times more than the oil, w/w) for loading on a soxhlet extractor (30 cm long and 6.5 cm diameter or more). The cold percolation of extractor with hexane removes non polar impurities such as ocimene. However, warm hexane percolation of Soxhlet extractor with an increasing proportion of ethylacetate upto 0.1 to 2% gave mainly dihydrotagetone rich fractions. The fractions were monitored on TLC plate and the desired fractions were combined and solvent was removed under vacuum to afford sweet smelling dihydrotagetone rich fractions (38 to 43% w/w or more depending upon the % of dihydrotagetone in tagetes oil) which were finally purified on silica gel column and the column was eluted with an increasing amount of hexane/ethyl acetate (100:0 to 95:5). The fractions having same $R_f$ were combined and solvent was removed under pressure to afford dihydrotagetone (4) (18 to 24% w/w or more depending upon the % of dihydrotagetone in tagetes oil) as a liquid with 99% purity (by GC); $R_f$=0.68 (2.5% ethylacetate in hexane); IR (film) $\lambda$max 2992, 1715, 1463, 1367, 913 cm$^{-1}$; $^1$H NMR $\delta$ 5.81–5.68 (m, 1H, 2-CH), 4.97–4.91 (t, 2H, 1-CH$_2$), 2.75–2.68 (m, 1H,3-CH), 2.46–2.35 (m, 1H, 7-CH), 2.32–2.01 (m, 4H, 4-CH$_2$ and 6-CH$_2$), 1.26–1.25(d, 3H, 10-CH$_3$), 1.03–0.99 and 0.92–0.87 (2d, 6H, 8-CH$_3$ and 9-CH$_3$); EIMS m/z 154 [M]$^+$ (1.8), 139 (1.7), 112 (1.4), 97 (31.8), 56 (14.7), 42 (12.8), 85(84.1), 57(100%), 58 (65.4). On the basis of above spectral data and comparing it with reported literature (Thappa, R. K., Agarwal, S. G., Kalia, N. K., Ramesh, K. and kapoor, R., J. Essentail Oil Research, 5(4), 375–379 (1993)), the liquid was identified as dihydrotagetone (4).

Example II

STR1##.

Figure 2:
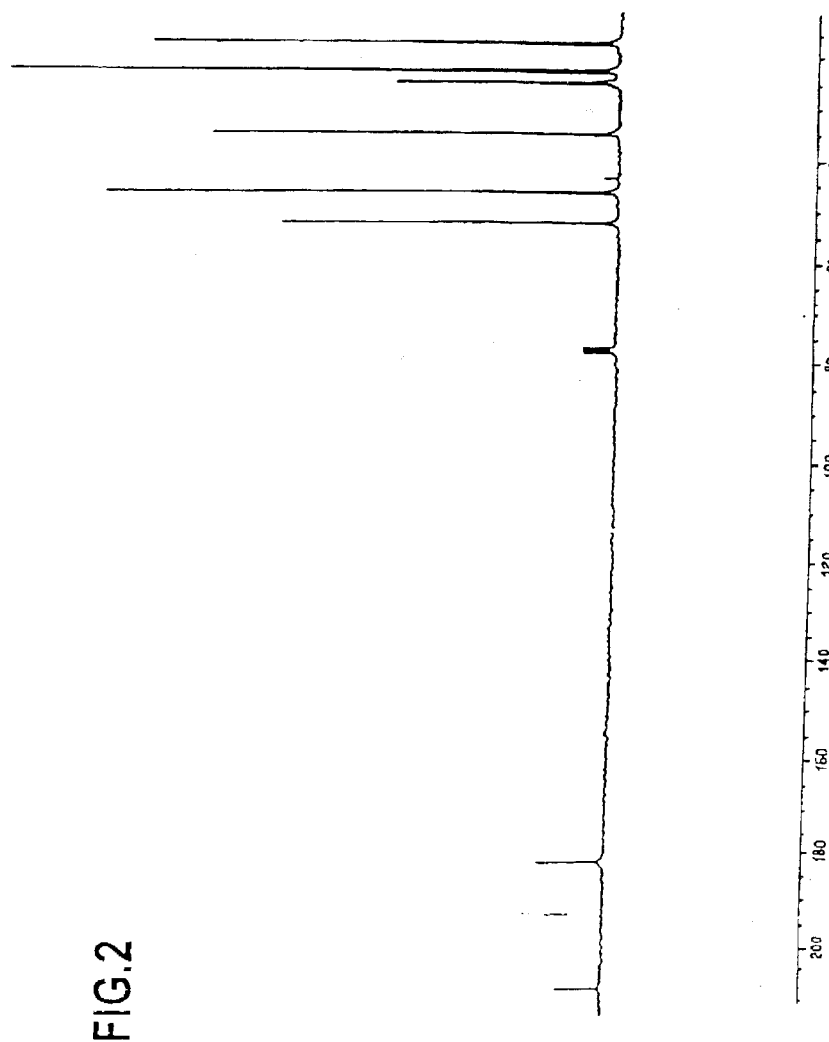
FIG. 2 is $^{13}$C NMR (75.4 MHz) spectra of 2,6-dimethyl-4-oxo-heptanoic acid (in CDCl$_3$) of the reaction product of Example I containing the compound having the structure: ##STR1##.

Synthesis of 2,6-dimethyl-4-oxo-heptanoic acid (3):

(i) (by conventional method): To a vigorously stirred solution of dihydrotagetone (4) (5 g, 33 mmole) in 1,4-dioxane-water (250 mL, 4:1) is added potassium carbonate (7 g,) followed by powdered potassium metaperiodate (15 g, 70 mmol) and then 0.25 g of powdered potassium permanganate. The remaining powdered potassium metaperiodate (35 g, 163.6 mmole) and potassium permnaganate (0.4–0.6 g) was added in small fractions within 30–40 minutes. The reaction mixture was left at room temperature for overnight and the solution, which was initially deep purple turned into light brown solution. The mixture was made alkaline with 10% potassium hydroxide and filtered and then residue was further washed with aqueous-dioxane mixture. The filtrate and washings were combined and the dioxane was evaporated under reduced pressure. The aqueous layer was extracted with ethylacetate (15 mL×2) to remove unwanted impurities. The aqueous layer was cooled at 4–8° C. and acidified with dilute acid and then extracted with ethylacetate (3×25 mL). The ethylacetate layers were then combined and washed with saturated sodium bisulphate (to destroy the excess permanganate), sodium chloride (3×15 m), dried over anhydrous sodium sulphate and filtered. The solvent was removed to afford a crude liquid which was loaded on silica gel column and the column was eluted with an increasing amount of hexane/ethyl acetate (100:0 to 95:5). The fractions were monitored on TLC plate and the desired fractions were combined and solvent was removed under vacuum to afford 2,6-dimethyl-4-oxo-heptanoic acid in 68% yield as a viscous liquid; $R_f$=0.69 (toluene:ethylacetate:methanol::6.5:3.5:0.1 mL); IR (film) $\lambda$max 2958, 1709, 1465, 1376, 937 cm$^{-1}$; $^1$H NMR $\delta$ 10.53 (s, 1H, COOH), 3.03–2.94 (m, 1H, 2-CH), 2.91–2.82 (m, 1H, 6-CH), 2.50–2.06 (m, 4H, 3-CH$_2$ and 5-CH$_2$), 1.23–1.20 (d, 3H, 9-CH$_3$), 0.99–0.97 and 0.92–0.90 (2d, 6H, 7-CH$_3$ and 8-CH$_3$)(FIG. 1); $^{13}$C NMR 208.66 (COOH, C-1), 181.94 (C=O, C-4), 51.71 (C-2), 45.89 (C-6), 34.39 (C-3), 24.54 (C-5), 22.39 (2×C-7 and C-8), 16.73 (C-9) (FIG. 2).

(ii) (by microwave method): A mixture of dihydrotagetone (4) (3.53 g, 22.92 mmole), sodium bicarbonate (1.8 g, 21.43 mmole), sodium metaperiodate (22.84 g, 106.78 mmole), potassium permanganate (0.65 g, 4.11 mmole), alumina (0.8–1.2 g) and THF-water or acetone-water (20 mL, 1:3) was taken in a 250 ml Erlenmeyer flask fitted with a loose funnel at the top. The flask was shaken well for a while and then placed inside a microwave oven (Kenstar) operating at medium power (600 W) and irradiated for 2–20 minutes in parts. After completion of the reaction (monitored by TLC), the contents of the flask were poured into saturated solution of sodium bisulphite to destroy excess permanganate and resulting mixture was passed through a bed of Celite and further washed with aqueous acetone (40 mL×3, 3:1). The filtrate and washings were combined and the solution concentrated under reduced pressure to remove acetone. The mixture was cooled to 0 to 8° C. and acidified with dilute acid and then extracted with ethylacetate (3×25 mL). The ethylacetate layers were then combined, washed with saturated sodium bisulphite and sodium chloride (3×15 mL), dried over anhydrous sodium sulphate and then filtered. The solvent was removed to afford a crude product which was purified on silica column as above which afforded 2,6-dimethyl-4-oxo-heptanoic acid (3) in 81% yield as a viscous liquid. The physical and spectral data was found similar as above (Example II-i).

Example III

STR2##.

Figure 3:
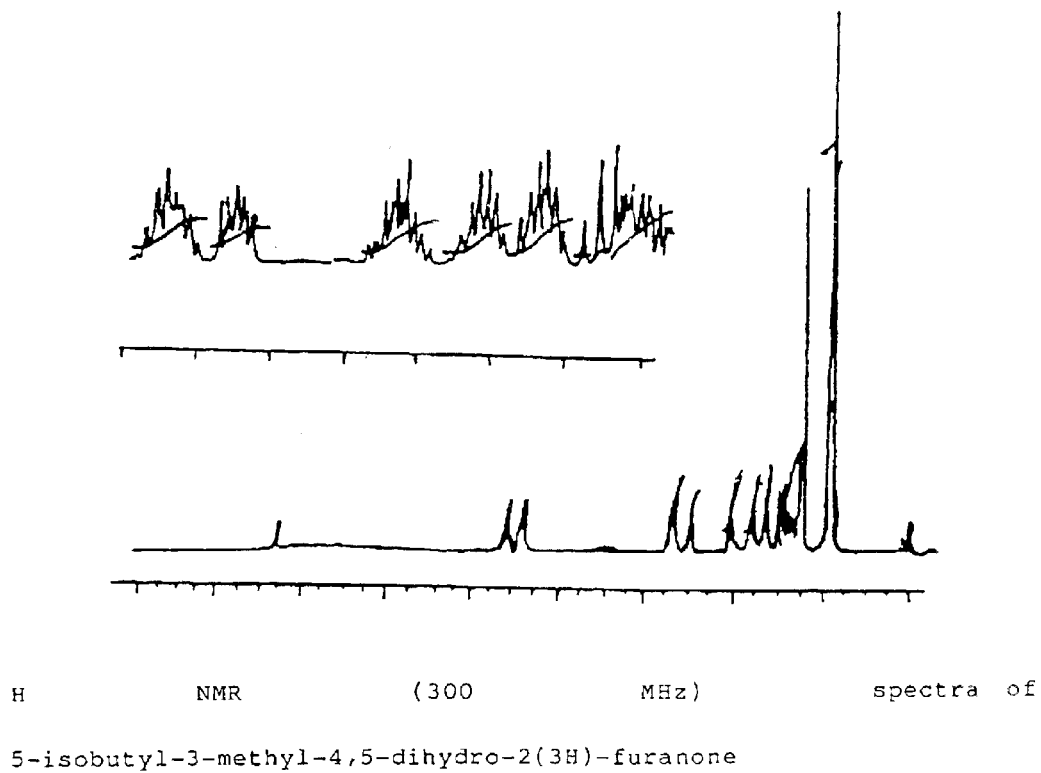
FIG. 3 is $^1$H NMR (300 MHz) spectra of 5-isobutyl-3-methyl-4,5-dihydro-2(3H)-furanone (in CDCl$_3$) of the reaction product of Example II containing the compound having the structure: ##STR2##.
Figure 6:
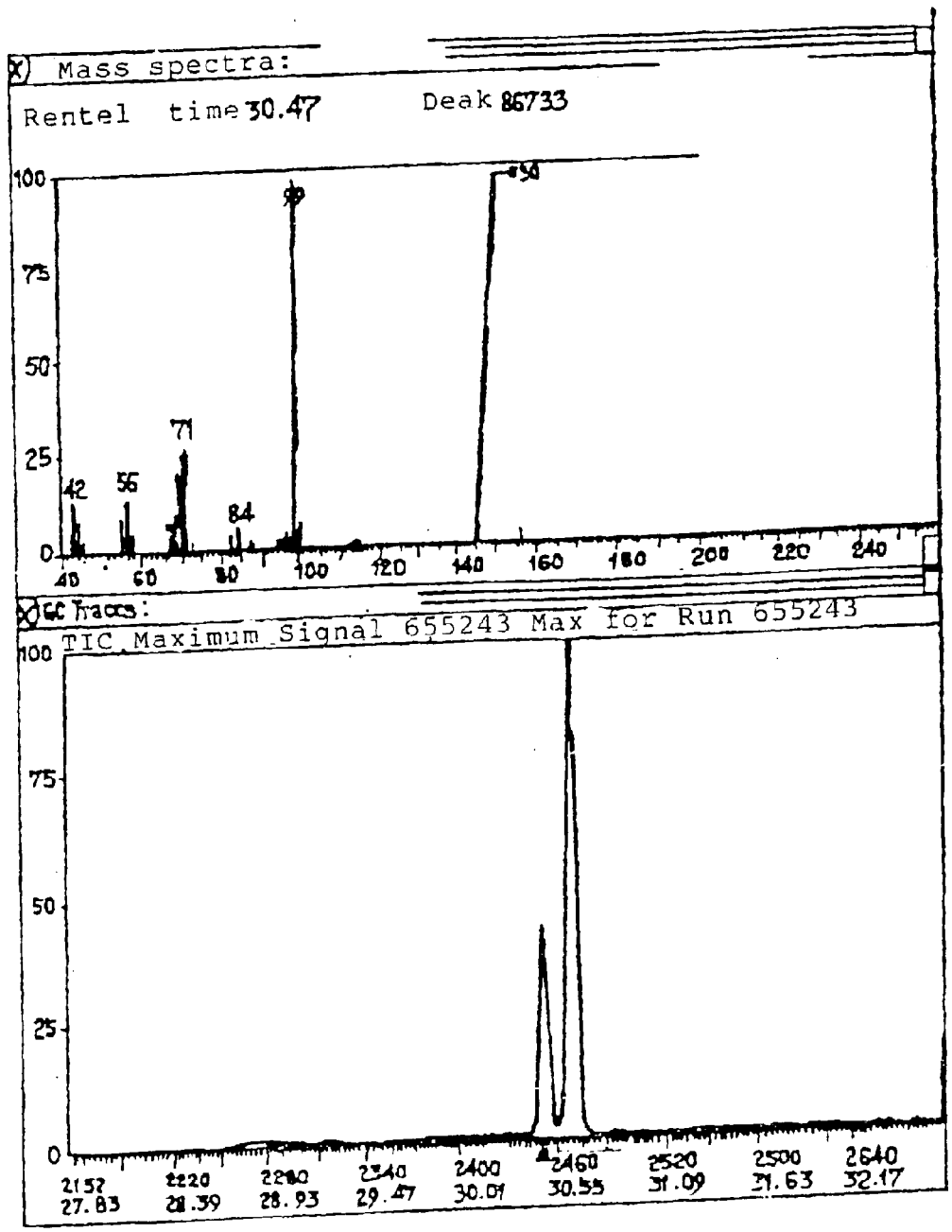
FIG. 6 is the electro spray (ES) mass spectrum of 5-isobutyl-3-methyl-4,5-dihydro-2(3H)-furanone (MW 156) of the reaction product of Example II containing the compound having the structure: ##STR2##.

Synthesis of 5-isobutyl-3-methyl-4,5-dihydro-2(3H)-furanone (4-isobutyl-2-methyl-4-butanolide) (1):

A cold solution (−5 to 8° C.) of sodium borohydride (0.6 g) in 2N-sodiumhydroxide (1.5 mL) was added dropwise very slowly to a stirred solution of 2,6-dimethyl-4-oxo-heptanoic acid (3) (1.0 g) in methanol (20 mL) and stirring was continued overnight. Methanol was evaporated and more water (3–4 mL) was added to the residue and the mixture was once again cooled to −5 to 0° C. and then acidified with cold dilute hydrochloric acid and then extracted with ether (3×50 mL). The combined extracts were washed with brine, dried (Na$_2$SO$_4$) and then concentrated to give a crude liquid which was loaded on silica gel column and the column was eluted with an increasing amount of hexane/ethyl acetate (100:0 to 95:5). The fractions were monitored on TLC plate and then the desired fractions were combined and solvent was removed under vacuum to afford 4-isobutyl-2-methyl-4-butanolide (trans:cis=68:32 on NMR basis) of formula (1) in 76% yield as a colourless oil with coconut flavour; $R_f$=0.80 (10% ethylacetate in hexane); IR (film) $\lambda$max 2962, 1772, 1558, 1457, 1362, 1173, 1135, 1004, 1024, 926 cm$^{-1}$; $^1$H NMR $\delta$ 4.63–4.55 (dqd, 0.32H, cis-5-CH), 4.46–4.38 (dtd, 0.68H, trans-5-CH), 2.73–2.62 (m, 1H, 3-CH), 2.55–2.47 (m, 1H, 7-CH), 2.09–2.04 and 1.84–1.78 (2 m, 2H, 4-CH$_2$), 1.67–1.61 and 1.50–1.41 (2 m, 2H, 6-CH$_2$), 1.36–1.26 and 1.27–1.25 (2d, 3H, 10-CH$_3$), 0.96–0.95 and 0.94–0.93 (2d, 6H, 8-CH$_3$ & 9-CH$_3$) (FIG. 3); $^{13}$C NMR $\delta$ 179.42 (d, C-2), 76.55 (d, C-5), 44.43 (d, C-3), 37.69 (s, C-4), 35.69 (d, C-7), 33.77 (s, C-6), 21.92 (d, C-10), 15.65, 14.89 (2s, C-8 and C-9) (FIG. 4); GC of compound 1 appeared at $t_r$=30.24 and $t_r$=30.44 also confirms the presence of isomers (FIG. 5); EIMS m/z 156 [M]$^+$ (1.3), 99 (100%), 84 (5.4), 71 (28.5), 56 (14.7), 42 (12.8) (FIG. 6).

The main advantages of the present invention are:

1. A simple process for industrial scale purification of dihydrotagetone of formula (4) from oil of *Tagetes* species.
2. A simple process for proper utilization of dihydrotagetone of formula (4) into high valued products.

3. A simple process for the preparation of 2,6-dimethyl-4-oxo-heptanoic acid of formula (3) as a novel product with one chiral center. i.e. 2,6-dimethyl-4-oxo-heptanoic acid (3).
4. A simple process is obtained for rapid conversion of dihydrotagetone of formula of (4) into 2,6-dimethyl-4-oxo-heptanoic acid of of formula (3) in microwave oven ranging from 5–30 minutes where the rate of reaction is further accelerated by adding alumina as a catalyst.
5. A process for the preparation of 2,6-dimethyl-4-oxo-heptanoic acid of formula (3) in high yield as a multipurpose additive in food and tobacco products as its analogue 2,6-dimethyl-5-oxo-heptanoic acid (found as a constituent of an important Italo-Mitcham peppermint oil i.e. *Menthaxpiperita L*) has wide application in perfumery, flavour and pharmaceutical industry.
6. A simple process for the preparation for 5-isobutyl-3-methyl-4,5-dihydro-2(3H)-furanone of formula (1) in high yield and high purity.
7. A simple process for the preparation of 5-isobutyl-3-methyl-4,5-dihydro-2(3H)-furanone of formula (1) as an analogue of whisky lactone or oak lactone or querecus lactone of formula (1a).
8. A simple process for the preparation of 5-isobutyl-3-methyl-4,5-dihydro-2(3H)-furanone of formula (1)) as an analogue of coconut aldehyde (1b).
9. The use of 5-isobutyl-3-methyl-4,5-dihydro-2(3H)-furanone as a starting material which is capable of undergoing conversion into new kind of corresponding furans, cyclopetenones, butenolides and pyrrolidone or the like.
10. Providing a novel product i.e. 5-isobutyl-3-methyl-4,5-dihydro-2(3H)-furanone of formula (1) in sufficient quantity for its applications in perfumery flavour and pharmaceutical industries.

What is claimed is:

1. The compound 2,6-dimethyl-4-oxo-heptanoic acid.
2. Soft drink formulations comprising the compound 2,6-dimethyl-4-oxo-heptanoic acid in a desired and acceptable amount varying from ppm to mg along with other drink compositions.
3. Herbal formulations comprising the compound 2,6-dimethyl-4-oxo-heptanoic acid in a desired and acceptable amount varying from ppm to mg along with other herbal compositions.
4. Alcoholic beverage formulations comprising the compound 2,6-dimethyl-4-oxo-heptanoic acid in a desired and acceptable amount varying from ppm to mg along with other beverage compositions.
5. Confectionery formulations comprising the compound 2,6-dimethyl-4-oxo-heptanoic acid in a desired and acceptable amount varying from ppm to mg along with other confectionery compositions.
6. Tobacco product formulations comprising the compound 2,6-dimethyl-4-oxo-heptanoic acid in a desired and acceptable amount varying from ppm to mg along with other tobacco compositions.

* * * * *